United States Patent [19]

Sheridan

[11] Patent Number: 4,888,154
[45] Date of Patent: Dec. 19, 1989

[54] COMBINATION STRUCTURE FOR SAMPLING THE CONTENTS OF A REACTOR VESSEL INCLUDING PH MONITORING MEANS

[75] Inventor: Michael Sheridan, Old Bridge, N.J.
[73] Assignee: Ethylene Corp., Murray Hill, N.J.
[21] Appl. No.: 23,114
[22] Filed: Mar. 6, 1987
[51] Int. Cl.⁴ .................. G01N 1/14; G01N 27/56
[52] U.S. Cl. .................. 422/49; 73/863.61; 73/863.81; 73/863.83; 204/420; 204/433; 422/68; 422/100; 422/119; 435/291
[58] Field of Search .................. 422/68, 99, 100, 119, 422/49; 204/420, 433; 73/863.61, 863.81, 863.83; 435/291-294, 315

[56] References Cited

U.S. PATENT DOCUMENTS

| | | | |
|---|---|---|---|
| 2,884,365 | 4/1959 | DeBolt et al. | 204/433 |
| 3,647,632 | 3/1972 | Johnson et al. | 435/315 |
| 3,718,567 | 2/1973 | Haddad et al. | 204/433 |
| 3,803,921 | 4/1974 | Dieterich | 73/863.61 |
| 3,819,330 | 6/1974 | Creighton | 73/863.83 |
| 4,008,141 | 2/1977 | Kotani et al. | 204/433 |
| 4,594,903 | 6/1986 | Johnson | 73/863.81 X |
| 4,595,487 | 6/1986 | Nunlist | 204/433 |

Primary Examiner—Barry S. Richman
Assistant Examiner—Timothy M. McMahon
Attorney, Agent, or Firm—Charles E. Temko

[57] ABSTRACT

A device capable of being mounted in a small opening in a reactor vessel, after having been inserted through a manway, which permits the continuous sampling of the contents of the reactor during a reaction, and continuous monitoring of the pH factor or other characteristic of interest. Electrical probe replacement is possible without disconnecting the device from the reactor vessel, and requires only a minimum of down time.

3 Claims, 2 Drawing Sheets

COMBINATION STRUCTURE FOR SAMPLING THE CONTENTS OF A REACTOR VESSEL INCLUDING PH MONITORING MEANS

BACKGROUND OF THE INVENTION

This invention relates generally to the field of processing of fluid chemicals, and more particularly to an improved structure capable of installation within the confines of a reactor vessel for the purpose of permitting continuous sampling of a reacting batch of material, as well as continuous monitoring of the pH factor or any other characteristic of interest during the reacting of the mass.

Pilot plant reactors are generally quite small in capacity, in the order of 50 to 500 gallons, with the number of nozzles, or small openings, passing through the wall of the vessel being at an absolute premium. The vessel normally includes a larger sealable opening known as a manway, which does not necessarily imply that it is of sufficiently large diameter to permit the passage of technical personnel therethrough.

During a given reaction cycle, it is often desirable to sample the contents of the vessel to determine that the reaction is proceeding properly. It is also desirable to continuously monitor the pH of the reacting mass. Access for either or both of the above purposes can be made through a small opening or nozzle. Should the vessel have only a pair of such nozzles, the utilization of them for sampling purposes will preclude the introduction of additional material, when required, during the reaction process.

The use of baffles in the reactor of so-called "h" design is known, and serves to break up circular flow of the reactor contents and create vortexes for improved mixing.

SUMMARY OF THE INVENTION

Briefly stated, the invention contemplates the provision of an improved device which may be incorporated into the structure of an "h" baffle within a reactor vessel which will provide for both intermittent or continuous sampling of the reactor contents, and the continuous monitoring of the pH factor of such contents. The entire device may be conveniently inserted into the vessel through an open manway, and mounted in position through a single nozzle, or smaller opening. Once installed, the electric probe which comprises a part of the device may be removed for examination or replacement without total disassembly of the device, at the end of or prior to the commencement of a reaction cycle. Means is provided for ultrasonic cleaning of the operative end of the probe, as required, without any disassembly of the device.

BRIEF DESCRIPTION OF THE DRAWINGS

In the drawings, to which reference will be made in the specification, similar reference characters have been employed to designate corresponding parts throughout the several views.

DETAILED DESCRIPTION OF THE DISCLOSED EMBODIMENT

Figure 1:
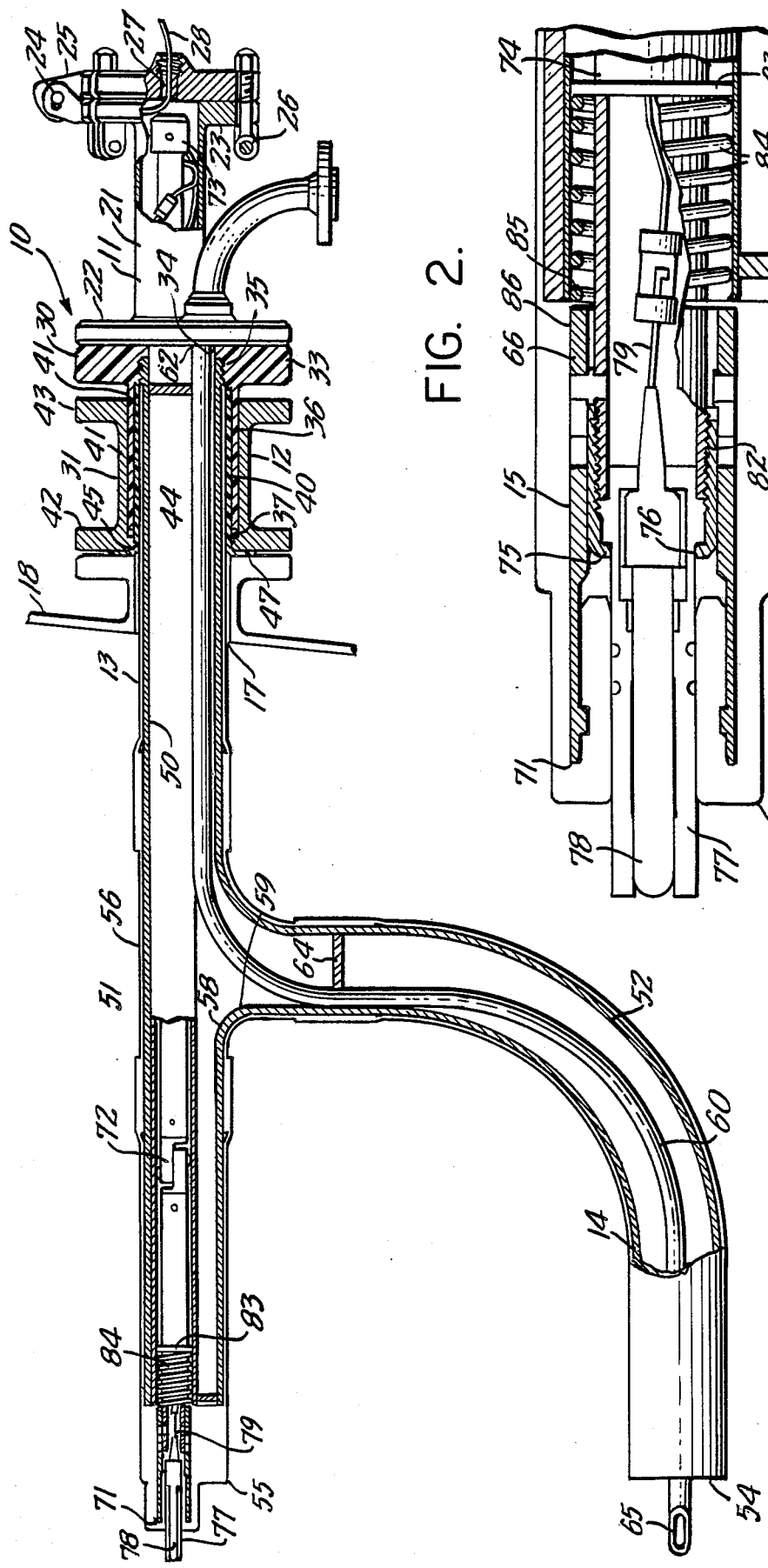
FIG. 1 is a schematic longitudinal sectional view of an embodiment of the invention, partly in elevation.
Figure 2:
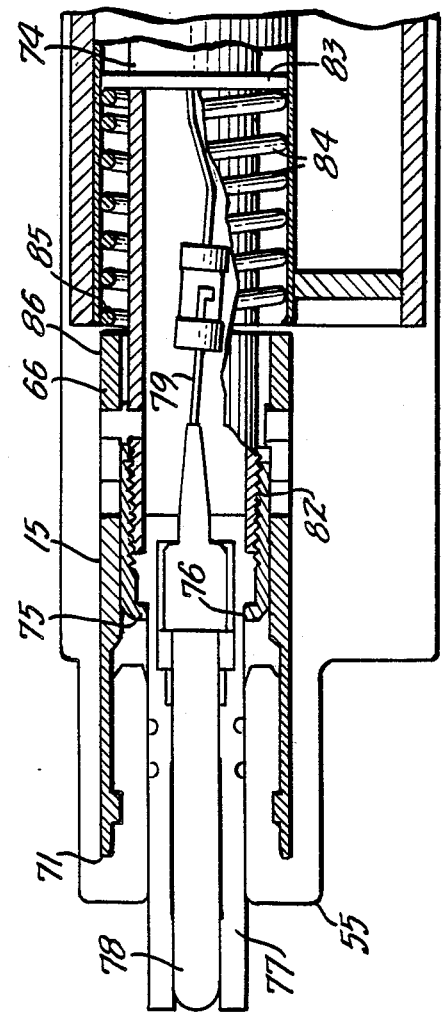
FIG. 2 is a view in elevation thereof, as seen from the lower portion of FIG. 1.
Figure 3:
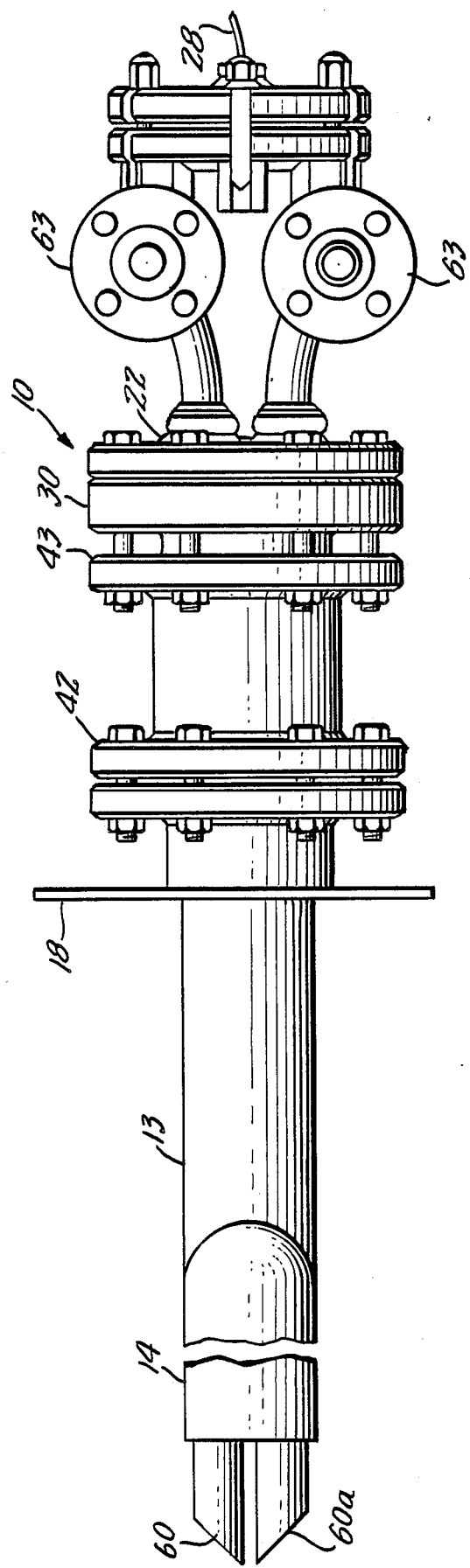

In accordance with the invention, the device, generally indicated by reference character 10, comprises broadly: an outer housing element 11, a vessel engaging element 12, an inner baffle element 13, fluid sampling means 14, and pH monitoring means 15. The device 10 is normally installed in a nozzle opening 17 of a reactor vessel 18.

The outer housing element 11 is preferably formed as a metallic casting, and includes an axially oriented tube 21 extending between an inner flanged end 22 and an outer flanged end 23. The end 23 is provided with hinged means 24 which mounts a pivotally oriented cap 25 having locking means 26. The cap 25 has a centrally disposed bore 27 for the passage of electrical leads 28.

The vessel engaging element 12 provides means for sealing the nozzle opening 17 when the device is installed. It includes first and second tubular elements 30 and 31, both of which are preferably formed of sintered polytetrafluoroethylene.

The first tubular element 30 includes a radially extending flange 33 having a centrally disposed bore 34 and a threaded counter bore 35, as well as an axially extending tubular shank 36 terminating in an end edge 37. The second tubular element 31 includes a tubular shank 41 terminating in first and second radially extending flanges 42 and 43. The flange 43 has a centrally disposed opening 44 which communicates with a cylindrical counter-bore 45 in the first radial flange 42. Penetrating the opening 44 and counter-bore 45 is a sleeve member 46, also of polytetrafluoroethylene, having a radially extending flange portion 47 at one end thereof.

The inner baffler element 13 performs the functions of a normal "h" baffle. It includes a metallic body 50 including a rectilinear leg 51 and a curvilinear leg 52. The curvilinear leg 52 merges with the rectilinear leg 51 within the vessel, so that they terminate in first and second outer ends 54 and 55, as well as first and second inner ends 58 and 59. A molded teflon enclosure 56 encloses the metallic body 50 to protect it against the deleterious effect of reacting chemicals.

The fluid sampling means 14 includes a pair of continuous suction and return tubes 60 and 60a having inner and outer ends 61 and 62, respectively. The outer end terminates in a flange 63 which may be connected to any suitable suction sampling device. The tube 60 is supported at convenient intervals by supports 64. The inner end 62 is provided with an angularly disposed opening 65 normally disposed within a reacting mass.

The pH monitoring means 15 is disposed within the rectilinear leg 51 and includes a tube 66 extending between an inner end 70 and an outer end 71 which connects with the axially oriented tube 21 of the outer housing element 11. Disposed within the tube is an articulated linkage 72 having an outer end 73 and an inner end 74. The inner end 74 includes a transversely extending end wall 75 having a central orifice 76 which accommodates a probe supporting element 77. The element 77 includes a longitudinally extending bore supporting in sealed relation a known electric pH probe 78 having electrical leads 79 extending within the leg 51. The element 77 is fixed to the inner end 74 by a threaded member 82. A spring engaging ring 83 cooperates with a coil spring 84, the inner end 85 of which bears upon a molded seat 86. This spring urges the linkage 72 outwardly when the pivotally mounted cap 25 is opened, to enable manual engagement of the outer end of the linkage 72 whereby to withdraw the probe 78.

The device is installed conveniently by disassembling the elements 11 through 13. The inner baffle element 13 is then passed through an open manway whereby the outer end thereof is passed through an open nozzle opening 17, and maintained in position while the vessel engaging element 12 is engaged therewith. The engagement of the tubular elements 30 and 31, and engagement of the threaded counter-bore 35 with the outer end of the body 50, secures the element 13 in position. The outer housing element 11 which is bonded to the flange 33 will then be properly positioned. The probe supporting element 77 may then be inserted within the rectilinear leg 51 to become properly seated, following which the cap 25 is closed and locked by the means 26. During this installation, the leads 28 will be passed through the cap for communication with monitoring equipment of known type (not shown).

Should the probe 78 require replacement, at the end of a reacting cycle, when the contents of the vessel are drained, the cap 25 is opened and the linkage 72 withdrawn along with the probe supporting element 77. The element 77, after examination, may be disassembled to permit the probe 78 to be removed and replaced.

It will thus be apparent that there has been provided a simple structure for both intermittent or continuous sampling of the contents of a reacting mass within a reactor vessel, and continuous monitoring of the pH factor or other characteristic. The entire device, in installed condition preempts only a single nozzle in the vessel, which is dedicated for this purpose. Since the device provides a baffling function, the normal "h" baffle may be eliminated without a corresponding loss of function.

We wish it to be understood that we do not consider the invention to be limited to the precise details of structure shown and set forth in this specification, for obvious modifications will occur to those skilled in the art to which the invention pertains.

We claim:

1. A combination structure for installation within a reactor vessel for sampling the reacting contents of the vessel and continuous monitoring of the pH factor of said contents, said structure comprising: an outer housing element, a vessel engaging element, and an inner baffle element; said inner baffle element being of "h" tubular configuration, and including a rectilinear leg and a curvilinear leg, said rectilinear leg having an outer end projecting through an opening in said vessel, said vessel engaging element engaging said outer end and maintaining said outer ends in fixed condition relative to said opening, said outer housing element being mounted upon said vessel engaging element; a fluid sampling conduit carried within said curvilinear leg, an inner end of which is positioned to lie within a reacting mass in said vessel, and an outer end of which is adapted to communicate with suction means; a pH monitoring means including a rectilinear tube disposed within said rectilinear leg, and having an inner end positioned to lie within said reacting mass, and an outer end extending outwardly through said opening in said vessel; an elongated linkage positioned within said rectilinear tube and having an inner end adjacent said inner end of said tube and an outer end projecting outwardly of said outer end of said tube; and a pH monitoring probe carried by said inner end of said linkage and electrically communicating with said outer end of said linkage.

2. A combination structure in accordance with claim 1, in which said linkage is articulated to facilitate the manual withdrawal thereof from said tube.

3. A combination structure in accordance with claim 1, further comprising resilient means urging said linkage outwardly of said rectilinear tube to facilitate the manual removal thereof.

* * * * *